(12) United States Patent
Kawano et al.

(10) Patent No.: US 9,073,845 B2
(45) Date of Patent: Jul. 7, 2015

(54) METHOD FOR PRODUCING ACROLEIN AND ACRYLIC ACID WITH A FIXED-BED MULTITUBULAR REACTOR

(71) Applicant: Nippon Shokubai Co., Ltd., Osaka (JP)

(72) Inventors: Tomoatsu Kawano, Hyogo (JP); Hideo Onodera, Hyogo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 14/383,966

(22) PCT Filed: Mar. 28, 2013

(86) PCT No.: PCT/JP2013/059304
§ 371 (c)(1),
(2) Date: Sep. 9, 2014

(87) PCT Pub. No.: WO2013/147041
PCT Pub. Date: Oct. 3, 2013

(65) Prior Publication Data
US 2015/0045581 A1      Feb. 12, 2015

(30) Foreign Application Priority Data

Mar. 30, 2012  (JP) ................................ 2012-078621

(51) Int. Cl.
| | | |
|---|---|---|
| *C07C 51/16* | (2006.01) | |
| *C07C 45/00* | (2006.01) | |
| *C07C 51/25* | (2006.01) | |
| *C07C 45/35* | (2006.01) | |
| *B01J 23/887* | (2006.01) | |
| *B01J 27/192* | (2006.01) | |
| *B01J 23/04* | (2006.01) | |
| *B01J 23/745* | (2006.01) | |
| *B01J 23/75* | (2006.01) | |
| *B01J 23/755* | (2006.01) | |

(52) U.S. Cl.
CPC ............... *C07C 51/252* (2013.01); *C07C 45/35* (2013.01); *B01J 23/8876* (2013.01); *B01J 27/192* (2013.01); *B01J 23/04* (2013.01); *B01J 23/745* (2013.01); *B01J 23/75* (2013.01); *B01J 23/755* (2013.01)

(58) Field of Classification Search
None
See application file for complete search history.

(56) References Cited

U.S. PATENT DOCUMENTS

| | | |
|---|---|---|
| 6,632,965 B1 | 10/2003 | Tanimoto et al. |
| 2003/0006026 A1 | 1/2003 | Matsumoto et al. |
| 2005/0033093 A1 | 2/2005 | Teshigahara et al. |
| 2005/0159620 A1 | 7/2005 | Teshigahara et al. |
| 2006/0211885 A1 | 9/2006 | Yoo et al. |
| 2007/0003460 A1 | 1/2007 | Matsumoto et al. |
| 2008/0107583 A1 | 5/2008 | Teshigahara et al. |
| 2008/0119667 A1 | 5/2008 | Teshigahara et al. |
| 2008/0286186 A1 | 11/2008 | Teshigahara et al. |
| 2009/0247787 A1 | 10/2009 | Yoo et al. |
| 2010/0249455 A1* | 9/2010 | Tanimoto et al. ............. 562/545 |

FOREIGN PATENT DOCUMENTS

| | | |
|---|---|---|
| JP | 2000-202294 | 7/2000 |
| JP | 2001-48817 | 2/2001 |
| JP | 2003-1094 | 1/2003 |
| JP | 2003-220334 | 8/2003 |
| JP | 2005-186065 | 7/2005 |
| JP | 2005-187460 | 7/2005 |
| JP | 2008-535784 | 9/2008 |
| JP | 2008-231044 | 10/2008 |
| JP | 2011-246384 | 12/2011 |

OTHER PUBLICATIONS

International Search Report issued Jul. 2, 2013 in International (PCT) Application No. PCT/JP2013/059304.

* cited by examiner

*Primary Examiner* — Yevegeny Valenrod
(74) *Attorney, Agent, or Firm* — Wenderoth, Lind & Ponack, L.L.P.

(57) ABSTRACT

This invention provides a method for producing acrolein and/or acrylic acid by catalytic gas-phase oxidation, which method makes it possible to carry out a continuous operation steadily for a long period of time while a high yield is maintained.

This method is characterized by comprising filling each of reaction tubes of a fixed-bed multitubular reactor with at least two species of catalysts each of which essentially comprises, as catalytically active components, oxide of molybdenum, oxide of bismuth and oxide of iron and/or composite oxide of at least two of said elements, said at least two species of catalysts being different in the ratio of D1/D2, D1 denoting the proportion of the total pore volume of pores whose pore diameter falls within the range of at least 0.03 μm and less than 0.3 μm to the total pore volume of the whole pores, and D2 denoting the proportion of the total pore volume of pores whose pore diameter falls within the range of at least 0.3 μm and at most 3 μm to the total pore volume of the whole pores, in such a manner that at least two reaction zones are formed axially in each of the reaction tubes.

15 Claims, No Drawings

US 9,073,845 B2

METHOD FOR PRODUCING ACROLEIN AND ACRYLIC ACID WITH A FIXED-BED MULTITUBULAR REACTOR

TECHNOLOGICAL FIELD

This invention relates to a method for producing acrolein and acrylic acid by catalytic gas-phase oxidation reaction of propylene with a fixed-bed multitubular reactor. In more detail, this invention relates to a method for producing acrolein and acrylic acid by catalytic gas-phase oxidation reaction of propylene with a fixed-bed multitubular reactor, reaction tube of which is filled with two or more catalyst layers.

BACKGROUND ART

Industrial-scale catalytic as phase oxidation reaction generally uses a fixed-bed reactor in which a starting compound-containing gas is made to pass through a reaction tube filled with catalyst, and is thus allowed to react. In particular for the production of (meth)acrolein and (meth)acrylic acid by catalytic gas-phase oxidation reaction of propylene, propane, isobutylene, etc., as a raw material compound, there has widely been employed a catalytic gas-phase oxidation reaction with a fixed bed multitubular reactor which is filled with solid particulate heterogeneous catalyst. Solid particulate heterogeneous catalyst which is to be used for this purpose generally includes a molded catalyst (unsupported catalyst) which is composed of active ingredients which have been molded into a specific geometric shape and a supported catalyst which is composed of a carrier material which has a geometric shape like that of molded catalyst and which has been coated with active ingredients (Patent Document 1).

There have been proposed methods for producing acrolein and acrylic acid with a high yield by catalytic gas-phase oxidation reaction of propylene, with a fixed-bed multitubular reactor which is filled with solid particulate heterogeneous catalyst as mentioned above. Most of such proposals relate to molybdenum-bismuth catalysts each of which mainly comprises molybdenum and bismuth which are used in the above-mentioned reaction, in detail to the composition, shape, physical properties of the catalysts and how to produce the same (Patent Documents 2, 3, and the like). There have also been made some proposals which relate to how to fill reaction tubes of a fixed-bed multitubular reactor with catalyst (Patent Documents 4, 5, 6 and 7).

CITATION LIST

Patent Literature Documents

Patent Document 1: Japanese Patent Application KOKAI Publication No. 2003-1094
Patent Document 2: Japanese Patent Application KOKAI Publication No. 2003-220334
Patent Document 3: Japanese Patent Application KOKAI Publication No. 2005-186065
Patent Document 4: Japanese Patent Application KOKAI Publication No. 2001-48817
Patent Document 5: Japanese PCT Application KOHYO Publication No. 2008-535784
Patent Document 6: Japanese Patent Application KOKAI Publication No. 2008-231044
Patent Document 7: Japanese Patent Application KOKAI Publication No. 2005-187460

SUMMARY OF INVENTION

Technical Problem

When worked on industrial scale, however, the as above-mentioned publicly known methods still leave room for improvement in respect to the yield, catalyst life, etc., of acrolein and acrylic acid of interest.

The problem to be solved by this invention is how to provide a method for producing acrolein and acrylic acid, by which a continuous operation can be carried out steadily for a long period of time in gas-phase catalytic oxidation of propylene while a high yield is maintained.

Solution to Problem

In order to solve the above-mentioned problem, the inventors of this invention made a detailed study about catalysts which might be usable for catalytic gas phase oxidation and on how to fill reaction tubes of a fixed-bed multitubular reactor with catalyst. As a result, they have found out that, when reaction tubes of a fixed-bed multitubular reactor are filled with at least two species of catalysts which are different in pore size distribution, and each of which comprises molybdenum, iron and bismuth as essential components, the desired products are favorably affected with regard to their performance such as yield, catalyst life, etc. This invention thus provides a method for producing acrolein and acrylic acid stably for a long period of time while a high yield is maintained, which method comprises filling each of reaction tubes of a fixed-bed multitubular reactor with at least two species of catalysts each of which comprises, as catalytically active components, oxide of molybdenum, oxide of iron and oxide of bismuth and/or composite oxide of at least two of said elements, said at least two species of catalysts being different in the ratio of D1/D2. D1 denoting the proportion of the total pore volume of pores whose pore diameter falls within the range of at least 0.03 µm and less than 0.3 µm to the total pore volume of the whole pores, and D2 denoting the proportion of the total pore volume of pores whose pore diameter falls within the range of at least 0.3 µm and at most 3 µm to the total pore volume of the whole pores, in such a manner that at least two reaction zones are formed axially in each of the reaction tubes.

Advantageous Effects of Invention

When reaction tubes of a fixed-bed multitubular reactor are filled with catalyst in the above-mentioned manner, this invention produces effects as follows:
(1) Acrolein and acrylic acid are obtained with a high yield;
(2) Catalyst can be used stably for a long period of time; and
(3) Acrolein and acrylic acid are obtained stably with a high yield from reaction under heavy load conditions such as a high concentration of raw material or a high space velocity.

DESCRIPTION OF EMBODIMENTS

In the following, this invention is explained in more detail. The scope of this invention is, however, not limited by the following explanation, but may be changed appropriately when this invention is to be worked, so long as the essence of this invention is not adversely influenced.

This invention relates to a method for producing acrolein and acrylic acid by the catalytic gas-phase oxidation of propylene with molecular oxygen by a fixed-bed multitubular reactor, which method comprises filling each of reaction tubes of a fixed-bed multitubular reactor with at least two species of catalysts each of which essentially comprises, as catalytically active components, oxide of molybdenum, oxide of bismuth and oxide of iron and/or composite oxide of at least two of said elements, said at least two species of catalysts being different in the ratio of D1/D2, D1 denoting the proportion of the total pore volume of pores whose pore diameter falls within the range of at least 0.03 μm and less than 0.3 μm to the total pore volume of the whole pores, and D2 denoting the proportion of the total pore volume of pores whose pore diameter falls within the range of at least 0.3 μm and at most 3 μm to the total pore volume of the whole pores, in such a manner that at least two reaction zones are formed axially in each of the reaction tubes.

No particular limitation is to be placed on fixed-bed multitubular reactor for this invention. Any type that has been generally employed for catalytic gas-phase oxidation is usable so long as the same is filled with catalyst in the above-mentioned manner. For instance, those which are conventionally known such as single reactor and tandem reactor can be suitably employed.

Gas-phase oxidation catalyst which is usable for this invention essentially comprises molybdenum, iron and bismuth, as catalytically active components, and suitably comprises a catalytically active component of formula (1) as follows:

$$Mo_{12}Bi_aFe_bA_cB_dC_eD_fO_x \qquad (1)$$

wherein Mo is molybdenum; Bi is bismuth; Fe is iron; A is at least one species of element selected from the group consisting of cobalt and nickel; B is at least one species of element selected from the group consisting of alkali metals, alkaline earth metals and thallium; C is at least one species of element selected from the group consisting of tungsten, silicon, aluminum, zirconium and titanium; D is at least one species of element selected from the group consisting of phosphorus, tellurium, antimony, tin, cerium, lead, niobium, manganese, arsenic, boron and zinc; and O is oxygen, and a, b, c, d, e, f and x each denote atomic rate of Bi, Fe, A, B, C, D and O, and $0<a\le10$, $0<b\le20$, $2\le c\le20$, $0<d\le10$, $0\le e\le30$, $0\le f\le4$, and x is a value, determined by the state of oxidation of each of the elements. Catalysts which comprise active components of the above formula (1) wherein B is at least one species of element selected from alkali metals, and $0.1\le a\le8$, $0.1\le b\le10$, $2\le c\le12$, and $0.1<d\le3$ is preferred.

Catalysts of this invention may be prepared by methods which are generally employed for the preparation of catalysts of this type, e.g., by a method as follows.

There is no particular limitation to be placed on starting materials which are usable for the catalytically active components of this invention. For example, oxides, hydroxides or salts (ammonium salts, nitrates, carbonates, sulfates, chlorides or organic acid salts) which contain each of the component elements, aqueous solution or sol of the same, compounds which contain two or more of the component elements, or combination of the same are usable. Among them, ammonium salts and nitrates are preferred.

Firstly, starting material for the catalytically active component as mentioned above is dissolved or suspended, for instance in water, to make an aqueous solution or an aqueous slurry (hereinafter sometimes referred to as "starting material mixture liquid").

Starting material mixture liquid as mentioned above can be prepared by any method that is usually employed for the preparation of catalyst of this kind. For example, one may prepare aqueous solutions or aqueous slurries which respectively contain starting materials for the above-mentioned catalytically active components, and mix the same with one another. Otherwise, one may prepare two or more aqueous solutions or aqueous slurries for each of starting materials for the catalytically active components, and divide the aqueous solutions or slurries and mix the resultant divisions with one another. No limitation is to be placed on the condition of mixing (order of mixing, temperature, pressure, pH, etc.) of starting materials for the catalytically active components.

Thus obtained starting material mixture liquid is used in a conventional supporting process, in the form of a liquid as the same has been heat-treated. Otherwise, a catalytic precursor in the form of a solid may be prepared from said starting material mixture liquid, through a drying process (primary drying process) by such a method as heating or pressure reduction, for use in supporting process or molding process which is mentioned later.

In order that a catalytic precursor may be prepared by heat drying in the primary drying process, a starting material mixture liquid may be either dried by evaporation to make a cake-like catalytic precursor, or dried by a spray dryer or a drum dryer to make a powdery catalytic precursor, or heated in an air stream with a box-type dryer, a tunnel dryer or the like to make a block or flake catalytic precursor. Otherwise, a cake-like solid which has been prepared by the drying of a starting material mixture liquid by evaporation may be further heated in an air stream with a box-type dryer, a tunnel dryer or the like to make a block or flake catalytic precursor.

In order that a solid catalytic precursor may be prepared by drying under reduced pressure in the primary drying process, a vacuum dryer for example may be used to obtain a block or powdery catalytic precursor.

Furthermore, a solid catalytic precursor which has been prepared by the above-mentioned primary drying process may be uninterruptedly calcined to make a catalytic precursor.

Thus obtained catalytic precursor may be pulverized or classified where necessary, to make a powdery catalytic precursor with a moderate particle size. In that case, there is no particular limitation on the particle size of the powder of catalytic precursor. Nevertheless, in order that good moldability may be achieved for the molding process which is mentioned later, the particle size should be 500 μm or less, preferably 300 μm or less, more desirably 150 μm or less.

The catalyst usable in this invention is to be used as a molded catalyst or a supported catalyst. Molded catalyst and supported catalyst are respectively prepared by the following methods. Molded catalyst is obtained by the molding of the above-mentioned catalytic precursor or a mixture of the above-mentioned catalytic precursor and a powdery inert carrier into a specific shape by extrusion molding or tablet molding.

In extrusion molding or tablet molding, the shape is not limited in particular. Any shape will do, including spherical, cylindrical, ring, and amorphous shape. If spherical, it does not need to be a perfect sphere but has only to be substantially spherical. Also in the case of cylindrical or ring shape, the cross section does not need to be a true circle but has only to be substantially circular.

Supported catalyst is prepared by the evaporation drying method which comprises applying or adhering, while heating, a starting material mixture liquid, not dried but kept in the form of an aqueous solution or an aqueous slurry, to a desired inert carrier which has a specific shape, the starting material mixture liquid being thus dried and supported. Alternatively, by the granulation method which comprises making the above-mentioned powder of catalytic precursor, or a powder of the same which has further been dried or calcined, supported on an inert carrier. In particular preferable is a granulation method by which catalytic precursor is made supported on an inert carrier by the centrifugal flow coating method as described in Japanese Patent Application KOKAI. Publication No. S63-200839, the rolling granulation method as described in Japanese Patent Application KOKAI Publication No. H10-28877, or by the rocking mixer method as described in Japanese Patent Application KOKAI Publication No. 2004-136267.

Examples of inert carrier to be used for molded catalyst or supported catalyst include alumina, silica, silica-alumina, titania, magnesia, steatite, cordierite, silica-magnesia, silicon carbide, silicon nitride, zeolite, and the like. For molded catalyst, powdery inert carrier will do. In that case, there is no particular limitation on the particle size. In order that good moldability may be achieved, the particle size is suitably 500 μm or less, preferably 300 μm or less, more desirably 150 μm or less. For supported catalyst, the above-mentioned inert carrier substance is molded into a specific shape to be used as a carrier. Thus molded carrier may have any publicly known shape including spherical, cylindrical or ring shape without any particular limitation.

In the molding process and the supporting process, adjuvant or binder may be used so that moldability and supportability may be improved. Examples of the same include organic compounds such as ethylene glycol, glycerin, propionic acid, maleic acid, benzyl alcohol, propyl alcohol, butyl alcohol and phenols; and water, nitric acid, ammonium nitrate, ammonium carbonate and urea.

In order to improve its mechanical strength, the catalyst of this invention may contain glass fiber or ceramic fiber which is generally known as a reinforcement, or fiber made from inorganic material such as silica, alumina, silicon carbide and silicon nitride. Inorganic fiber as mentioned above may be added by any method without particular limitation, as long as the inorganic fiber is uniformly dispersed in the catalyst. For example, inorganic fiber may be added to a starting material mixture liquid, or inorganic fiber may be mixed with a solid catalytic precursor in the molding process.

Molded body which has been obtained by the above-mentioned molding process or supported body which has been obtained by the above-mentioned supporting process is sent to the calcination process after having passed through the secondary drying process where necessary.

In the secondary drying process, molded body or supported body is dried by heating in an atmosphere of molecular oxygen-containing gas or of an inert gas such as molecular nitrogen and carbon dioxide or of a mixture of the same, with a box-type dryer or a tunnel dryer which is generally used, specifically at a drying temperature of 100-350° C. preferably 130-300° C., more desirably 150-250° C., for 1-24 hours, preferably 2-20 hours, more desirably 3-16 hours.

In the calcination process, a conventional box-type oven or tunnel oven may be used with no particular limitation. Calcination temperature is 350-600° C., preferably 400-550° C., more desirably 420-500° C. Calcination time is 1-15 hours, preferably 2-10 hours. Calcination is conducted in an air atmosphere, an air flow, in an atmosphere of inert gas (e.g., molecular nitrogen or carbon dioxide), or in an inert gas flow. Calcination in an atmosphere of molecular oxygen-containing gas is preferred. As a molecular oxygen-containing gas, air is preferably used.

Calcination is conducted after, or without, the above-mentioned secondary drying process. A supported body which has been made from catalytic precursor which had been prepared by the previous calcination of catalytically active components does not necessarily need to undergo a calcination process, but has only to pass through the above-mentioned secondary drying process so long as binder or adjuvant which might have been used in the supporting process can be removed.

Catalysts to be used in this invention which are different in pore size distribution in catalytically active component can be prepared by methods such as (1) a method of adjusting the ratio between ammonium ion and nitrate ion which are contained, in the starting material mixture liquid, (2) a method of adjusting the size of ca key or block solid, or adjusting the drying condition such as temperature, the species of atmospheric gas or flow rate, in the heating treatment in a gas stream with a box-type dryer, a tunnel dryer or the like in the above-mentioned primary drying step, or (3) a method of adjusting the particle size of powdery catalytic precursor in the above-mentioned pulverizing process.

The above-mentioned method (1) of adjusting the ratio between ammonium ion and nitrate ion which are contained in the starting material mixture liquid comprises, for example, changing the starting materials, or adding, to the starting material mixture liquid, a substance which contains nitrate ion or ammonium ion such as nitric acid, ammonia and ammonium nitrate. When the ratio of the number of moles of ammonium ion to the number of moles of nitrate ion is 1.0 or higher, D1/D2 ratio is relatively large. If said ratio is less than 0.8, D1/D2 ratio is relatively small.

In the above-mentioned method (2) by which to prepare catalysts which are different in pore size distribution by adjusting the drying condition in the primary drying process, when the size of solid is so adjusted that the distance between any two ends of the solid may be at most 30 mm, preferably less than 20 mm, D1/D2 ratio would be relatively small. When, on the other hand, the size is adjusted so that said distance may be at least 30 mm, preferably at least 50 mm, D1/D2 ratio would be relatively large. In the method (2), won the other hand, when the species of atmospheric gas or flow rate is to be adjusted, the method comprises adjusting the ratio (V/W) of the amount V [L, (standardstate)/min.] of the atmospheric gas to be introduced into the dryer which has a concentration of molecular oxygen of 5-25%, to the mass W (kg) of the above-mentioned starting material mixture liquid or the mass W (kg) of the above-mentioned catalyst precursor such as cakey solid which has been prepared by the evaporation drying of starting material mixture liquid. For example, when the ratio (V/W) of the amount of molecular oxygen-containing gas as an atmospheric gas in the primary drying process to the mass of the starting material mixture liquid or the mass W of the cakey solid which has been prepared by the evaporation drying of starting material mixture liquid is adjusted to be at least 400, preferably at least 500, D1/D2 ratio would be relatively small. When the ratio of V/W is adjusted to be less than 200, preferably less than 100, D1/D2 ratio would be relatively large.

In the above-mentioned method (3) of adjusting the particle size of powder of catalytic precursor in the pulverizing process, when the particle size of powder is less than 50 μm, preferably less than 20 μm, D1/D2 ratio would be relatively large. When said particle size is 100 μm or more, preferably 150 μm or more, D1/D2 ratio would be relatively small.

The above-mentioned methods (1), (2) and (3) for adjusting the pore size distribution in catalytically active component may be carried out either separately or in combination of two or three.

In this invention, there is no particular limitation on how to fill and arrange the catalyst, so long as each of reaction tubes of a fixed-bed multitubular reactor is filled with at least two species of catalysts which are different in the ratio of D1/D2, D1 denoting the proportion of the total pore volume of pores whose pore diameter falls within the range of at least 0.03 μm and less than 0.3 μm to the total pore volume of the whole pores, and D2 denoting the proportion of the total pore volume of pores whose pore diameter falls within the range of at least 0.3 μm and at most 3 μm to the total pore volume of the whole pores, in such a manner that layers are formed axially in each of the reaction tubes.

In this invention, when each of reaction tubes of a fixed-bed multitubular reactor is filled, on the gas inlet side, with a catalyst which has a small D1/D2 ratio, and on the gas outlet side with a catalyst which has a large D1/D2 ratio, the yield of acrolein and acrylic acid as the desired products improves as compared with the case where the D1/D2 ratio is constant. When, on the other hand, each of reaction tubes of a fixed-bed multitubular reactor is filled, on the gas inlet side, with a catalyst which has a large D1/D2 ratio, and on the has outlet side with a catalyst which has a small D1/D2 ratio, catalyst life improves as compared with the case where the D1/D2 ratio is constant. This invention can thus improve either the yield of acrolein and acrylic acid as the desired products or catalyst life, by arranging two or more catalysts which are different in D1/D2 ratio in reaction tubes.

In addition to the improvement in catalyst life, this invention achieves a very remarkable improvement in the yield of acrolein and acrylic acid. In this respect, each of reaction tubes of a fixed-bed multitubular reactor is preferably filled, on the gas inlet, side, with a catalyst which has a small D1/D2 ratio, and on the as outlet side with a catalyst which has a large D1/D2 ratio.

In this invention, D1/D2 ratio is acceptably 0.1-8, preferably 0.2-6, more desirably 0.3-5.

There is also no particular limitation on the number of reaction zones. For industrial purpose, two or three reaction zones are enough to produce effects as desired. The dividing proportion of value is dependent on oxidation reaction conditions, or on the composition, shape or the size of catalyst with which to fill each layer. It would therefore be necessary to choose the dividing proportion appropriately so that optimal activity and selectivity may be attained as a whole.

When reaction tubes of a fixed-bed multitubular reactor are each filled with a catalyst in such a manner that three or more reaction zones are formed, it is not necessary to arrange the catalyst so that the D1/D2 ratio may increase progressively from the gas inlet side toward the gas outlet, or may decrease progressively from the gas inlet side toward the gas outlet. Catalyst has only to be arranged so that, in at least two of the reaction zones, the pore size distribution of the filled catalyst satisfies the above-mentioned relationship. The objective of this invention is achieved also when the catalyst is arranged so that the D1/D2 ratio may firstly decrease and then increase, or firstly increase and then decrease, from the gas inlet side toward the gas outlet side.

This invention uses a fixed-bed multitubular reactor each of whose reaction tubes is filled with a catalyst for gas phase oxidation in the above-mentioned manner, for the purpose of the production of acrolein and acrylic acid by catalytic gas phase oxidation of propylene with molecular oxygen or a molecular oxygen-containing gas. Raw material for reaction is propylene or propylene-containing gas.

The method of this invention is suitably applicable, for example, as a first stage of two-stage catalytic gas phase oxidation by which to produce acrylic acid from propylene as a starting material. There is no particular limitation placed on propylene as a raw material, examples of which include polymer grade propylene or chemical grade propylene, or propylene-containing mixed gas which is produced by the dehydrogenation or oxidative dehydrogenation of propane. This mixed gas may also contain air or oxygen where necessary.

There is no particular limitation on the reaction condition for the method of this invention; any reaction condition that has been generally employed in this type of reaction is usable. For example, a normal raw material as for reaction (e.g., a mixed gas which comprises 1 to 15% by volume, preferably 4 to 12% by volume, of propylene, 0.5 to 25% by volume, preferably 2 to 20% by volume, of molecular oxygen, 0 to 30% by volume, preferably 0 to 25% by volume, of water vapor, and the balance of inert gas such as nitrogen) is suitably brought into contact with oxidation catalyst at a temperature ranging from 280 to 430° C., preferably from 280 to 400° C. under a reaction pressure of 13.1 to 1.0 MPa, and at a space velocity of propylene of 100-600 $hr^{-1}$ (standard condition), preferably 120-300 $hr^{-1}$ (standard condition).

This invention is explained in detail by Examples below. The scope of this invention is, however, not to be limited by those Examples. In the following, "part(s) by mass" may be referred to as "part(s)" for the sake of simplicity. Conversion and yield have been calculated in accordance with formulae below:

Conversion (mol %)=[(the number of moles of propylene which has reacted)/(the number of moles of propylene which has been fed)]×100

Yield (mol %)=[(the number of moles of acrolein and acrylic acid which have been formed)/(the number of moles of propylene which has been fed)]×100

Measurement of Pore Volume and Pore Size Distribution

The pore volume and pore size distribution of catalyst in this invention have been given as pore volume and pore size distribution per unit mass of catalyst, by measurement in a range of pore size from 0.003 to 200 μm with a mercury intrusion porosimeter (trademark: "AutoPore IV 9500", manufactured by Micromeritics Corporation), at an average pressure elevation rate of 0.005-0.3 MPa/sec.

Catalyst Production Example 1

Preparation of Catalyst (1)

There were dissolved 341 parts of cobalt nitrate and 82 parts of nickel nitrate in 500 parts of deionized water. Furthermore, 92 parts of ferric nitrate and 128 parts of bismuth nitrate were dissolved in an aqueous solution of nitric acid which, comprised 75 parts of 65% by weight of nitric acid and 300 parts of deionized water. Besides, 400 parts of ammonium paramolybdate and 5.1 parts of ammonium paratungstate were added to 1500 parts of deionized water, and the resultant mixture was stirred to make a solution. Into thus obtained aqueous solution, the above-mentioned two aqueous solutions which had been prepared separately were dipped to make a mixture. To thus obtained mixture, an aqueous solution of 1.9 parts of potassium nitrate dissolved in 30 parts of deionized water was added to make a suspension. Thus obtained suspension was stirred with heating until the same became clayish, and, was thereafter left to cool naturally to give a solid matter. This solid in an amount of 50 kg was brought into a tunnel dryer, into which air was introduced at a flow rate of 2500 L (standard state)/min. (V/W=50). After dried at, 185° C. for 15 hours, the solid matter was pulverized to the size of 300 μm or less to give a powder of catalytic precursor. A rolling granulator was charged with 340 parts of alumina spherical carrier having an average particle diameter of 5.0 mm, and was then gradually fed with the powder of catalyst precursor, along with a 20 mass % aqueous solution of ammonium nitrate as a binder, so that the powder of catalyst precursor might be supported on the carrier. Subsequent heat treatment at 470° C. for six hours in an air atmosphere gave catalyst (1). This catalyst (1) was composed of metallic elements, except for oxygen and carrier, as follows:

$$Mo_{12}Bi_{1.4}Ni_{1.5}Co_{6.2}Fe_{1.2}W_{0.1}K_{0.1}$$

Calculation based on the following equation indicated that the carrying amount of catalyst (1) was 140% by mass.

Carrying amount (mass %)=[(mass of catalyst−mass of carrier used)/(mass of carrier used)]×100

Catalyst Production Example 2

Preparation of Catalyst (2)

Catalyst Production Example 1 was repeated except that the flow rate of air to be introduced into the tunnel dryer was changed to give a V/W ratio of 400, and that the solid matter was (fried at 180° C. for 14 hours, and, thus, catalyst (2) was obtained.

Catalyst Production Example 3

Preparation of Catalyst (3)

Catalyst Production Example 1 was repeated except that the flow rate of air to be introduced into the tunnel dryer was changed to give a V/W ratio of 600, and that the solid matter was dried at 180° C. for 14 hours, and, thus, catalyst (3) was obtained.

Catalyst Production Example 4

Preparation of Catalyst (4)

Catalyst Production Example 1 was repeated except that the size of solid matter which had been produced by a heat treatment of suspension was adjusted so that the distance between any two ends might be less than 100 mm, that the flow rate of air to be introduced into the tunnel dryer was changed to give a V/W ratio of 100, and that the solid matter was dried at 180° C. for 15 hours, and, thus, catalyst (4) was obtained.

Catalyst Production Example 5

Preparation of Catalyst (5)

Catalyst Production Example 1 was repeated except that the flow rate of air to be introduced into the tunnel dryer was changed to give a V/W ratio of 300, and that the solid matter after dried was pulverized to the size of 120 μm or less, and, thus, catalyst (5) was obtained.

Table 1 shows the preparation conditions, the carrying amount and D1/D2 ratio, of catalysts (1) to (5).

Example 1

A reactor which comprised 24 steel-made reaction tubes, each having a full length of 3000 mm and an inner diameter of 25 mm, which were covered with a shell in which to flow a heating medium was vertically prepared. Firstly catalyst (2) was allowed to fall from above the top of reaction tube, from the direction of reaction gas inlet side toward the outlet side, so as to make a layer length of 900 mm, and subsequently catalyst (1) so as to make a layer length of 2000 mm, so that reaction tubes were each filled with reaction zones having a total layer length of 2900 mm.

A gas mixture which comprised 8.0%, by volume of propylene, 15.4% by volume of oxygen, 9.1% by volume of water vapor and a balance of inert gas such as nitrogen was introduced into reaction tubes which had each been filled with catalyst, at a space velocity of propylene of 125 h$^{-1}$ (standard state) while the temperature of heating medium was kept at 320° C., and, thus, a propylene-oxidizing reaction was conducted. Results are shown in Table 2.

Example 2

A propylene-oxidizing reaction was conducted in the same manner as in Example 1 except that reaction tubes were each filled, from the direction of reaction gas inlet side toward the outlet side, firstly with catalyst (1) to make a layer length of 800 mm, and subsequently with catalyst (2) to make a layer length of 2100 mm. Results are shown in Table 2.

Example 3

A propylene-oxidizing reaction was conducted in the same manner as in Example 1 except that reaction tubes were each filled, from the direction of reaction gas inlet side toward the outlet side, firstly with catalyst (3) to make a layer length of 600 mm, subsequently with catalyst (2) to make a layer length of 700 mm, and, further with catalyst (1) to make a layer length of 1600 mm. Results are shown in Table 2.

Comparative Example 1

A propylene-oxidizing reaction was conducted in the same manner as in Example 1 except that reaction tubes were each filled only with catalyst (1) to make a layer length of 2900 mm. Results are shown in Table 2. As compared with Example 1, yield was low both when the initial 80 hours of oxidation reaction had passed, and when 4000 hours had passed, and the rate of reaction temperature elevation with time was large.

Comparative Example 2

A propylene-oxidizing reaction was conducted in the same manner as in Example 1 except that reaction tubes were each filled only with catalyst (2) to make a layer length of 2900 mm. Results are shown in Table 2. As compared with Example 1, yield was low both when the initial 80 hours of oxidation reaction had passed, and when 4000 hours had passed, and the rate of reaction temperature elevation with time was large.

Comparative Example 3

A propylene-oxidizing reaction was conducted in the same manner as in Example 1 except that reaction tubes were each filled only with catalyst (3) to make a layer length of 2900 mm. Results are shown in Table 2. As compared with Example 1, yield was low both when the initial 80 hours of oxidation reaction had passed, and when 4000 hours had passed, and the rate of reaction temperature elevation with time was large.

Example 4

A propylene-oxidizing reaction was conducted in the same manner as in Example 1 except that reaction tubes were each filled, from the direction of reaction gas inlet side toward the outlet side, firstly with catalyst (5) to make a layer length of 800 mm, and subsequently with catalyst (4) to make a layer length of 2100 mm. Results are shown in Table 2.

TABLE 1

| Catalyst | Drying conditions | Note | Carrying amount (mass %) | D1/D2 |
|---|---|---|---|---|
| (1) | V/W = 50, 185° C. 15 hours | | 140 | 4.1 |
| (2) | V/W = 400, 180° C. 14 hours | | 141 | 1.0 |
| (3) | V/W = 600, 180° C. 14 hours | | 139 | 0.4 |
| (4) | V/W = 100, 180° C. 15 hours | Distance between any two ends of the dried solid matter was less than 100 mm. | 142 | 4.0 |
| (5) | V/W = 300, 185° C. 15 hours | Powder of catalytic precursor was pulverized to the size of 120 μm or less. | 138 | 0.5 |

TABLE 2

| | Catalysts filled Gas inlet side → Gas outlet side (D1/D2) | Reaction time (Hr) | Reaction temperature (° C.) | Propylene conversion (mol %) | Yield of acrolein + acrylic acid (mol %) |
|---|---|---|---|---|---|
| Example 1 | Catalyst (2)/Catalyst (1) 900 mm/2000 mm (1.0/4.1) | 80 4000 | 320 333 | 97.8 97.7 | 93.3 93.2 |
| Example 2 | Catalyst (1)/Catalyst (2) 800 mm/2100 mm (4.1/1.0) | 80 4000 | 320 330 | 97.6 97.7 | 93.0 92.9 |
| Example 3 | Catalyst (3)/Catalyst (2)/ Catalyst (1) 600 mm/700 mm/1600 mm (0.4/1.0/4.1) | 80 4000 | 320 332 | 97.8 97.8 | 93.5 93.4 |
| Comparative Example 1 | Catalyst (1) 2900 mm (4.1) | 80 4000 | 320 335 | 97.9 97.9 | 92.7 92.5 |
| Comparative Example 2 | Catalyst (2) 2900 mm (1.0) | 80 4000 | 320 336 | 97.6 97.5 | 92.5 92.6 |
| Comparative Example 3 | Catalyst (3) 2900 mm (0.4) | 80 4000 | 321 337 | 97.6 97.5 | 92.7 92.7 |
| Example 4 | Catalyst (5)/Catalyst (4) 800 mm/2100 mm (0.5/4.0) | 80 4000 | 320 333 | 97.7 97.7 | 93.4 93.3 |

The invention claimed is:

1. A method for producing acrolein and acrylic acid by the catalytic gas-phase oxidation of propylene with molecular oxygen or molecular oxygen-containing gas by a fixed-bed multitubular reactor which has been filled with catalyst, which method comprises filling each of reaction tubes of a fixed-bed multitubular reactor with at least two species of catalysts each of which essentially comprises, as catalytically active components, oxide of molybdenum, oxide of bismuth and oxide of iron and/or composite oxide of at least two of said elements, said at least two species of catalysts being different in the ratio of D1/D2, D1 denoting the proportion of the total pore volume of pores whose pore diameter falls within the range of at least 0.03 μm and less than 0.3 μm to the total pore volume of the whole pores, and D2 denoting the proportion of the total pore volume of pores whose pore diameter falls within the range of at least 0.3 μm and at most 3 μm to the total pore volume of the whole pores, in such a manner that at least two reaction zones are formed axially in each of the reaction tubes.

2. The method of claim 1 for producing acrolein and acrylic acid wherein said catalyst comprises a catalytically active component of formula (1) as follows:

$$Mo_{12}Bi_aFe_bA_cB_dC_eD_fO_x \quad (1)$$

wherein Mo is molybdenum; Bi is bismuth; Fe is iron; A is at least one species of element selected from the group consisting of cobalt and nickel; B is at least one species of element selected from the group consisting of alkali metals, alkaline earth metals and thallium; C is at least one species of element selected from the group consisting of tungsten, silicon, aluminum, zirconium and titanium; D is at least one species of element selected from the group consisting of phosphorus, tellurium, antimony, tin, cerium, lead, niobium, manganese, arsenic, boron and zinc; and O is oxygen, and a, b, c, d, e, f and x each denote atomic rate of Bi, Fe, A, B, C, D and O, and $0<a\leq10$, $0<b\leq20$, $2\leq c\leq20$, $0<d\leq10$, $0\leq e\leq30$, $0\leq f\leq4$, and x is a value which is determined by the state of oxidation of each of the elements.

3. The method of claim 1 for producing acrolein and acrylic acid wherein said catalyst is a molded catalyst into which the above-mentioned catalytically active component has been molded.

4. The method of claim 1 for producing acrolein and acrylic acid wherein said catalyst is a supported catalyst in which the above-mentioned catalytically active component is supported on an inert carrier of a specific shape.

5. The method of claim 1 for producing acrolein and acrylic acid wherein each of reaction tubes of a fixed-bed multitubular reactor is filled, on the gas inlet side, with a catalyst which has a small D1/D2 ratio, and on the gas outlet side with a catalyst which has a large D1/D2 ratio.

6. The method of claim 1 for producing acrolein and acrylic acid wherein d1/d2 ratio is 0.1 to 8.

7. The method of claim 2 for producing acrolein and acrylic acid wherein said catalyst is a molded catalyst into which the above-mentioned catalytically active component has been molded.

8. The method of claim 2 for producing acrolein and acrylic acid wherein said catalyst is a supported catalyst in which the above-mentioned catalytically active component is supported on an inert carrier of a specific shape.

9. The method of claim 2 for producing acrolein and acrylic acid wherein each of reaction tubes of a fixed-bed multitubular reactor is filled, on the gas inlet side, with a catalyst which has a small D1/D2 ratio, and on the gas outlet side with a catalyst which has a large D1/D2 ratio.

10. The method of claim 3 for producing acrolein and acrylic acid wherein each of reaction tubes of a fixed-bed multitubular reactor is filled, on the gas inlet side, with a catalyst which has a small D1/D2 ratio, and on the gas outlet side with a catalyst which has a large D1/D2 ratio.

11. The method of claim 4 for producing acrolein and acrylic acid wherein each of reaction tubes of a fixed-bed multitubular reactor is filled, on the gas inlet side, with a catalyst which has a small D1/D2 ratio, and on the gas outlet side with a catalyst which has a large D1/D2 ratio.

12. The method of claim 2 for producing acrolein and acrylic acid wherein d1/d2 ratio is 0.1 to 8.

13. The method of claim 3 for producing acrolein and acrylic acid wherein d1/d2 ratio is 0.1 to 8.

14. The method of claim 4 for producing acrolein and acrylic acid wherein d1/d2 ratio is 0.1 to 8.

15. The method of claim 5 for producing acrolein and acrylic acid wherein d1/d2 ratio is 0.1 to 8.

* * * * *